United States Patent [19]

Katsumata et al.

[11] Patent Number: 5,236,831
[45] Date of Patent: Aug. 17, 1993

[54] AMINO ACID SYNTHESIS IN CORYNEBACTERIA AND BRERIBACTERIA USING E. COLI GENES

[75] Inventors: Ryoichi Katsumata; Akio Ozaki; Toru Mizukami, all of Tokyo; Motoko Kageyama, Numazu; Morimasa Yagisawa; Tamio Mizukami, both of Tokyo; Seiga Itoh, Sagamihara; Tetsuo Oka, Yokohama; Akira Furuya, Kawasaki, all of Japan

[73] Assignee: Kiowa Hakko Kogyo Co., Ltd., Tokyo, Japan

[21] Appl. No.: 474,648

[22] Filed: Feb. 2, 1990

Related U.S. Application Data

[63] Continuation of Ser. No. 787,010, Oct. 11, 1985, abandoned, which is a continuation of Ser. No. 504,243, Jun. 17, 1983, abandoned, which is a continuation-in-part of Ser. No. 454,059, Dec. 28, 1982, abandoned.

[30] Foreign Application Priority Data

Dec. 29, 1981 [JP] Japan ................................. 56-211908

[51] Int. Cl.⁵ ...................... C12P 13/19; C12P 13/04; C12P 13/08
[52] U.S. Cl. ................................. 435/106; 435/110; 435/115; 435/172.3; 435/252.32; 435/320.1
[58] Field of Search .................... 536/27; 435/71.2, 91, 435/170, 172.3, 183, 115, 110, 252.3, 252.32, 320.1, 840, 849, 843, 106; 935/6, 9, 22, 29, 38, 39, 59, 60, 61, 66, 72

[56] References Cited

U.S. PATENT DOCUMENTS

| | | | |
|---|---|---|---|
| 4,278,765 | 7/1981 | Debabov et al. | 435/172.3 |
| 4,304,863 | 12/1981 | Collins et al. | 435/172.3 |
| 4,342,832 | 8/1982 | Goeddel et al. | 435/172.3 |
| 4,347,318 | 8/1982 | Miwa et al. | 435/115 |
| 4,349,629 | 9/1982 | Carey et al. | 435/172.3 |
| 4,427,773 | 1/1984 | Tsuchida et al. | 435/110 |
| 4,489,160 | 12/1984 | Katsumata et al. | 435/253 |
| 4,500,640 | 2/1985 | Katsumata et al. | 435/253 |
| 4,560,654 | 12/1985 | Miwa et al. | 435/115 |

FOREIGN PATENT DOCUMENTS

| | | |
|---|---|---|
| 0030391 | 6/1981 | European Pat. Off. . |
| 0058889 | 9/1981 | European Pat. Off. . |
| 0063763 | 11/1982 | European Pat. Off. . |
| 0066129 | 12/1982 | European Pat. Off. . |
| 0071023. | 2/1983 | European Pat. Off. . |
| 0073062 | 3/1983 | European Pat. Off. . |
| 0077548 | 4/1983 | European Pat. Off. . |
| 0093611 | 11/1983 | European Pat. Off. . |
| 8109776 | 11/1981 | France . |
| 2076853 | 12/1981 | United Kingdom . |

OTHER PUBLICATIONS

Cossart et al., 1981, *NAR:* 9(21:339-347).
Shiio et al., 1970, *J. Biochem* 68:701-710.
Izui et al., 1981, *FEBS Letters,* 133: 311-315.
Miller, The Journal of Pediatrics, vol. 99, No. 1, pp. 1-15, Jul. 1981.
Schottel et al., 1981, J. Bacteriol., 146:360-368.
Moran et al., Nucleotide Sequences that Signal the Initiation of Transcription and Translation in Bacillus Subtilis, Mol. Gen. Genet., vol. 186 (1982) 339:46.
Ehrlich, DNA Cloning in Bacillus Subtilis, P.N.A.S. U.S.A., vol. 75, No. 3 (1978) 1433:6.

(List continued on next page.)

[57] ABSTRACT

Disclosed is a process for expressing a gene and producing a metabolic product formed by the gene by culturing a transformant microorganism carrying a recombinant DNA constructed of a DNA fragment having at least one gene to be expressed and a vector DNA, at least one of which is foreign to the host microorganism.

9 Claims, 2 Drawing Sheets

OTHER PUBLICATIONS

McLaughlin et al., Unique Features in the Ribosome Binding Site Sequence of the Gram-Positive Staphylococcus aureus β-Lactamase Gene, J. Biol. Chem., vol. 256, No. 21 (1991) Nov. 2, 1983:91.

Stallcup et al., Initiation of Protein Synthesis In Vitro by a Clostridial System, J. Biol. Chem., vol. 248, No. 9 (1973) 3209:15.

Goldfarb et al., Expression of Tn9-derived chloramphenicol resistance in Bacillus Subtilis, Nature, vol. 293 (1981) 309:11.

Goldfarb et al., Translational block to expression of the Escherichia Coli Tn9-derived chloramphenicol-resistance gene in Bacillus Subtilis, P.N.A.S. U.S.A., vol. 79 (1982) 5886:90.

Kreft et al., Recombinant Plasmids Capable of Replication in B. subtilis and E. coli., Mol. Gen. Genet., vol. 162 (1978) 59:67.

*Primary Examiner*—Richard A. Schwartz
*Assistant Examiner*—John LeGuyader
*Attorney, Agent, or Firm*—Fitzpatrick, Cella, Harper & Scinto

AMINO ACID SYNTHESIS IN CORYNEBACTERIA AND BRERIBACTERIA USING E. COLI GENES

This application is a continuation of U.S. application Ser. No. 787,010, filed Oct. 11, 1985, now abandoned, which is a continuation of U.S. application Ser. No. 504,243, filed Jun. 17, 1983, now abandoned, which is a continuation-in-part of U.S. application Ser. No. 454,059, filed Dec. 28, 1982, now abandoned.

BACKGROUND OF THE INVENTION

The present invention relates generally to a method for expressing a gene in a microorganism, and more specifically, to a method for expression of a gene by transforming a host microorganism belonging to the genus Corynebacterium or Brevibacterium with a recombinant DNA constructed of a DNA fragment containing at least one gene to be expressed and a vector DNA in which at least one of the DNAs is foreign to the host microorganism. Heretofore, recombinant DNA technology has been established using primarily *Escherichia coli* as the host microorganism. So far the production of peptides such as somatostatin, insulin, human growth hormone, human interferon-α and human interferon-β or vaccines such as foot-and-mouth disease vaccine has been reported, and *Escherichia coli* is considered to be adequate as a host microorganism for the expression of these highly physiologically-active peptides or vaccines. In order to achieve enhanced production, secretion out of the cells and glycosylation of a desired protein or to avoid contamination with intracellular toxins, host-vector systems in yeasts or *Bacillus subtilis* have also been developed.

For the production of physiologically active substances such as peptides, proteins and the like, the microorganisms mentioned above, for which recombinant DNA technology has already been established, may be satisfactorily employed. However, for the industrial mass production of substances such as amino acids, nucleic acids, vitamins, antibiotics and the like by recombinant DNA technology, those host microorganisms heretofor used are not applicable, and suitable technology for those microorganisms conventionally used for the production of the particular substance has to be developed.

*Corynebacterium glutamicum* was used first for the industrial production of amino acids. Subsequently, the industrial production of amino acids such as glutamic acid, lysine, alanine, histidine, tryptophan, tyrosine, phenylalanine, threonine, isoleucine, valine, leucine, glutamine, proline, arginine and the like has been developed using coryneform bacteria including those microorganisms classified in the genus Corynebacterium. As of the present, most amino acids are now commercially produced using microorganisms.

Therefore, application of recombinant DNA technology to these microorganisms is considered to be very important to improve the production of amino acids and the like.

Recombinant DNA technology generally consists of the following steps:

(1) Fragmentation of a DNA containing a desired gene with restriction endonucleases;
(2) Linearization of a vector DNA with the same restriction endonuclease;
(3) Construction of a recombinant DNA by mixing the DNA fragments with linearized vector plasmid mentioned above for annealing and ligating both DNAs with a DNA ligase;
(4) Introduction of the recombinant DNA into a host microorganism (transformation); and
(5) Selection and cloning of a recombinant containing the desired gene.

Successful construction of a recombinant strain is, of course, dependent upon the efficiency of each step. Therefore it is necessary to determine and improve the efficiency of each step to obtain transformants with a reasonable efficacy. Even if a desired gene is successfully introduced into a host, it is very difficult to express it because of various barriers to the expression of foreign genes. Kagaku to Seibutsu 18, 110–118 (1978).

Microorganisms belonging to the genus Corynebacterium or Brevibacterium have not yet been successfully used as a host to introduce desired genes or vectors foreign to the host and to express the desired genes. To develop recombinant DNA technology using host microorganisms belonging to the genus Corynebacterium or Brevibacterium, the construction of autonomously replicable vectors having selectable markers and suitable cloning sites for many genes is required as well as the establishment of efficient transformation systems. Moreover, a method for overcoming the barriers mentioned above is also required.

In furthermore of the foregoing, plasmid vectors autonomously replicable in microorganisms belonging to the genus Corynebacterium or Brevibacterium and having appropriate selectable markers and suitable cloning sites have been constructed by common inventors and highly efficient transformation systems have been developed. These are described in U.S. patent application Ser. No. 368,035 and U.S. Ser. No. 368,034, both filed Apr. 13, 1982 and Japanese Patent Application Nos. 58186/81, 58187/81 and 65777/81. It has now been found that when a DNA fragment containing a foreign gene involved in the biosynthesis of amino acids is inserted into such a plasmid vector by in vitro recombinant DNA technology (U.S. Pat. No. 4,237,224) and *Corynebacterium glutamicum* L-22 or its derivatives are transformed with the recombinant DNA by the transformation system mentioned above, it is possible to express the foreign gene in the host microorganism and increase the production of such useful substances such as amino acids and the like.

SUMMARY OF THE INVENTION

In accordance with the present invention, a method for expressing a gene comprises culturing in a medium a transformant obtained by transforming a host microorganism belonging to the genus Corynebacterium or Brevibacterium with a recombinant DNA wherein a DNA fragment containing at least one gene is inserted into a vector DNA and at least one of said DNAs is foreign to the host microorganism.

DNA fragments containing genes useful for the present invention are those derived from eukaryotes, prokaryotes, viruses, bacteriophages or plasmids and having at least one intact gene. The genes derived from eukaryotes are, for example, those coding for mammalian peptides such as human interferon, insulin and growth hormone. The genes derived from prokaryotes are, for example, those derived from bacteria belonging to the genus Escherichia, Corynebacterium, Brevibacterium, Bacillus, or Staphylococcus and involved in the metabolism and especially biosynthesis, of the bacteria. As used herein, "metabolism" or "biosynthesis" refers to the all cellular activities involved in the biosynthesis of amino acids, vitamins, nucleic acids or antibiotics. In the present invention, the genes responsible for the biosynthesis of amino acids such as glutamic acid, lysine or threonine are particularly preferred.

If the amino acid sequences of the desired peptides or proteins are known, the corresponding DNAs are synthesized and used in this invention. The synthesis of DNAs can be carried out according to the method described in K. Itakura et al., Science, 198, 1056 (1977).

Suitable vectors for the present invention are those which are compatible with the host microorganism and which are capable of being replicated in the host. Preferred examples of suitable vectors are the plasmids obtained from microorganisms belonging to the genus Corynebacterium and their derivatives, for example, the plasmids named pCG1 (U.S. patent application Ser. No. 346,867, filed Feb. 8, 1982), pCG2 (U.S. patent application Ser. No. 410,887, filed Aug. 24, 1982), pCG4 (U.S. patent application Ser. No. 368,035, filed Apr. 13, 1982), pCE53, pCE54, pCG11, pCB101 and pEthr1 U.S. patent application Ser. No. 450,359, filed Dec. 16, 1982.

Microorganisms harboring these plasmids have been deposited with the Fermentation Research Institute, Agency of Industrial Science and Technology, Chiba, Japan and the American Type Culture Collection, Rockville, Md., U.S.A. under the following accession numbers.

| Plasmid | FERM P- | ATCC |
|---------|---------|------|
| pCG1 | 5865 | 31808 |
| pCG2 | 5954 | 31832 |
| pCG4 | 5939 | 31830 |
| pCE54 | — | 39019 |
| pCG11 | — | 39022 |
| pCB101 | — | 39020 |
| pEthr1 | — | 39021 |

Of the foregoing plasmids, pCG11 and pCE54 are most preferred.

Plasmid pCG11 is a plasmid constructed by some of the present inventors and described in the aforementioned U.S. patent application Ser. No. 346,867. Plasmid pCG11 is prepared by inserting a BamHI fragment containing a gene responsible for resistance to streptomycin and/or spectinomycin (referred to as $Sm^R/Spec^R$ gene hereinafter) of plasmid pCG4 isolated from *Corynebacterium glutamicum* 225-250 (ATCC 31830, FERM P-5939) into the unique BglII cleavage site of plasmid pCG1 isolated from *Corynebacterium glutamicum* 225-57 (ATCC 31808, FERM P-5865) using the same cohesive ends of both fragments. Plasmid pCG11 is a plasmid having a molecular weight of about 6.8 Kb and a single cleavage site for BglII and PstI and gives $Sm^R/Spec^R$ phenotype.

Plasmid pCE54 can be prepared as follows. Plasmid pCG2 is isolated from the cultured cells of *Corynebacterium glutamicum* 225-218 (FERM P-5954, ATCC 31832) by the method described in the above application and plasmid pGA22 is isolated from the cultured cells of *Escherichia coli* by a conventional method. Both plasmid DNAs are digested completely with a restriction endonuclease which has a unique cleavage site in each molecule, for example, PstI to linearize the DNAs. The cohesive ends of both plasmids are annealed and ligated with T4 phage DNA ligase to make a composite molecule. Selection of the recombinant plasmid from the ligation mixture is carried out by isolating transformants of the genus Corynebacterium or Brevibacterium on the basis of drug-resistances derived from pGA22 and then analyzing the plasmids in the transformants.

Transformation with the DNA mixture is carried out using protoplasts of the genus Corynebacterium or Brevibacterium, and the method described in U.S. patent application Ser. No. 368,034, filed Apr. 13, 1982 and Japanese Patent Application Nos. 58187/81 and 65777/81. Among the genes responsible for drug resistance derived from pGA22, those except for the ampicillin-resistance gene (referred to as $Amp^R$ hereinafter) which is insertionally inactivated, i.e. the tetracycline (Tc), chloramphenicol (Cm) and kanamycin (Km)-resistance genes are used for selection. Transformants are recovered as a colony regenerated on a hypertonic agar medium containing a drug in a concentration wherein the recipient protoplasts not treated with the DNA can not regenerate to normal cells, that is, 0.4–1.6 μg/ml tetracycline, 2.5–5 μg/ml chloramphenicol or 100–800 μg/ml kanamycin. Alternatively, transformants are regenerated unselectively on a regeneration medium, and the resultant cells are scraped and resuspended, followed by the isolation of those cells growing on an agar medium containing a drug in a concentration wherein the recipient normal cells can not grow, that is, generally 0.5–4 μg/ml tetracycline. Some of the transformants resistant to tetracycline, chloramphenicol or kanamycin are simultaneously endowed with other drug-resistances derived from plasmid pGA22.

Plasmid DNAs in the transformants can be isolated from cultured cells of the transformants and purified according to the methods described in U.S. patent application Ser. No. 346,867 filed Feb. 8, 1982 and Japanese Patent Application Nos. 18101/81 and 65777/81. The structures of the DNAs can be determined by digesting them with various restriction endonucleases and analyzing the DNA fragments by agarose gel electrophoresis. The plasmid isolated from one of the transformants is named pCE54.

pCE54 is a plasmid having a molecular weight of about 14.5 Kb and only one cleavage site for EcoRI, SalI, SmaI and XhoI and gives the phenotypes of $Tc^R$, $Cm^R$ and $Km^R$. Since the cleavage site for XhoI is present in the $Km^R$ gene, selection by insertional inactivation (prevention of the expression of a gene by the insertion of a DNA fragment into the gene) is possible. Recovery of plasmids from the strains is carried out according to the methods described in U.S. patent applications Ser. No. 346,867, filed Feb. 8, 1982, Ser. No. 368,035 filed Apr. 13, 1982 and Ser. No. 410,887 filed Aug. 24, 1982 and Japanese Patent Application Nos. 18101/81, 58186/81 and 133557/81.

Preparation of a recombinant of a vector DNA with a DNA fragment containing a gene is carried out by conventional in vitro recombinant DNA technology, e.g. cleavage and joining of a donor DNA containing a desired gene to a vector DNA. DNAs can readily be cleaved with restriction endonucleases. A restriction endonuclease used in the in vitro recombinant DNA technology recognizes and cleaves at a specific base sequence on double stranded DNA of any organism. The recognition sequence differs with each restriction endonuclease. Therefore, a desired gene can be obtained as a DNA fragment without impairing the function for expression of the gene by using appropriate restriction endonucleases. The donor and vector DNA cut with the same restriction endonuclease have staggered cohesive ends which are complementary to each other or have blunt ends depending on the restriction enzyme used. In either case, both DNAs can be ligated by T4 phage DNA ligase (referred to as T4 ligase hereinafter) whenever the DNAs are cleaved with the same restriction endonuclease.

When the DNAs are cut with different restriction endonucleases, they can be combined after repairing the staggered ends to form blunt ends or after combining with the blunt ends, complementary homopolymer tails with a terminal transferase or oligonucleotide linker with a ligase. The latter is cleaved with a corresponding restriction endonuclease to expose cohesive ends. By such methods, a recombinant of a DNA fragment containing a desired gene and a vector DNA fragment is constructed.

The ligase reaction gives recombinants containing genes other than the desired genes. The desired recombinant DNA can be obtained by directly transforming a microorganism of the genus Corynebacterium or Brevibacterium with the DNA mixture, selecting the transformants having the phenotype derived from the desired gene and isolating the desired recombinant DNA from the cultured cells of the transformants. Instead of cloning the desired genes directly in a microorganism of the genus Corynebacterium or Brevibacterium, the desired genes can be cloned by using another host-vector system such as *Escherichia coli*. Then, they are recloned in vitro into a vector of the genus Corynebacterium or Brevibacterium to transform that microorganism and transformants containing the desired recombinant plasmid are selected as mentioned above.

The following references are helpful for the construction of recombinant DNA:

S. N. Cohen, et. al., U.S. Pat. No. 4,237,224;
Idenshi Sosa Jikkenho, edited by Yasuyuki Takagi, printed by Kodansha Scientific (1980);
Method in Enzymology 68, Recombinant DNA edited by Ray Wu, Academic Press, 1979

Microorganisms belonging to the genus Corynebacterium or Brevibacterium and which are competent for incorporating DNAs may be used as the host microorganisms in the present invention. Preferably, lysozyme-sensitive microorganisms such as those described in Japanese Patent Application No. 151464/81 and U.S. patent application Ser. No. 372,129 filed Apr. 27, 1982 are used. The following are examples of a suitable host microorganism.

|  | Accession Number | |
| --- | --- | --- |
|  | FERM P- | ATCC |
| *Corynebacterium glutamicum* L-15 | 5946 | 31834 |
| *Corynebacterium herculis* L-103 | 5947 | 31866 |
| *Brevibacterium divaricatum* L-204 | 5948 | 31867 |
| *Brevibacterium lactofermentum* L-312 | 5949 | 31868 |

In order to observe the guidelines for recombinant DNA experiments in Japan, only *Corynebacterium glutamicum* L-22 and its derivatives which are approved by the Science and Technology Agency in Japan are used in the examples of the present invention. However, those skilled in the art will appreciate from the following description that the invention is equally applicable to other microorganisms belonging to the genera Corynebacterium and Brevibacterium.

BRIEF DESCRIPTION OF THE DRAWINGS

In the accompanying drawings, forming a part of the specification.

DETAILED DESCRIPTION OF THE INVENTION

Figure 1:
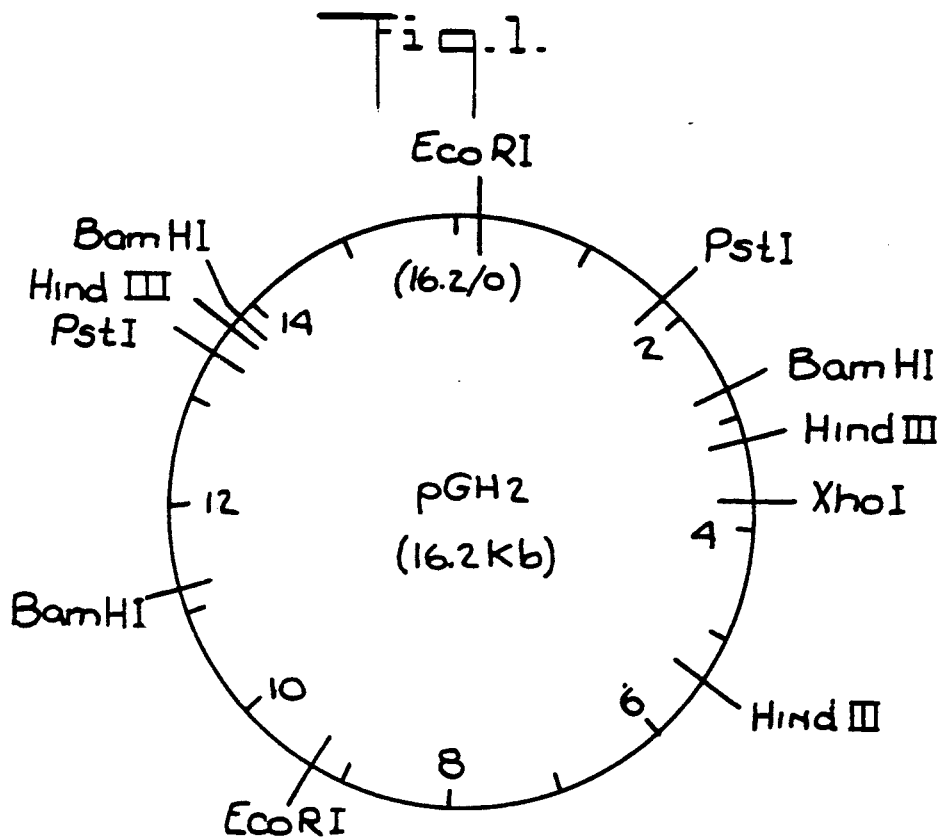
FIG. 1 is a cleavage map of the plasmid pGH2.

In accordance with the present invention transformation of the host microorganisms with recombinant DNAs is carried out by the following steps:
1) Preparation of protoplasts of cultured cells;
2) Transformation of the protoplast with a recombinant DNA;
3) Regeneration of the protoplast to normal cells and selection of a transformant;

These steps are described in detail below.

1) Preparation of protoplasts of cultured cells

The preparation of protoplasts is carried out by culturing a microorganism under conditions which render it sensitive to lysozyme, a lytic enzyme, and treating the cultured cells with lysozyme in a hypertonic solution to remove the cell wall. In order to render microbial cells sensitive to lysozyme, reagents inhibiting the synthesis of bacterial cell walls are used. For example, microbial cells sensitive to lysozyme are obtained by adding, during the log phase of growth, an amount of penicillin which does not inhibit or sub-inhibits the growth and then continuing culturing for several generations.

For culturing, any medium wherein the microorganism can grow may be used. For example, a nutrient medium NB (pH 7.2) consisting of 20 g/l powdered bouillon and 5 g/l yeast extract and a semi-synthetic medium SSM (pH 7.2) consisting of 10 g/l glucose, 4 g/l NH$_4$Cl, 2 g/l urea, 1 g/l yeast extract, 1 g/l KH$_2$PO$_4$, 3 g/l K$_2$HPO$_4$, 0.4 g/l MgCl$_2$.6H$_2$O, 10 mg/l FeSO$_4$.7H$_2$O, 0.2 mg/l MnSO$_4$.(4–6)H$_2$O, 0.9 mg/l ZnSO$_4$.7H$_2$O, 0.4 mg/l CuSO$_4$.5H$_2$O, 0.09 mg/l Na$_2$B$_4$O$_7$.10H$_2$O, 0.04 mg/l (NH$_4$)$_6$Mo$_7$O$_{24}$.4H$_2$O, 30 µg/l biotin, and 1 mg/l thiamine hydrochloride are used. Microbial cells are inoculated in the medium and culturing is carried out with shaking. The optical density (OD) of the culture medium at 660 nm is monitored with a colorimeter and penicillin, such as penicillin G, is added to the medium at an initial stage of the logarithmic growth phase (OD: 0.1–0.4) in a concentration of 0.1 to 2.0 U/ml. Culturing is then continued and at an OD value of 0.3–0.5, the cells are harvested and washed with the SSM medium. The washed cells are resuspended in a suitable hypertonic medium such as PFM medium (pH 7.0–8.5) wherein 0.4M sucrose and 0.01M MgCl$_2$.6H$_2$O are added to 2 fold diluted SSM medium, and RCG medium (pH 7.0–8.5) consisting of 5 g/l glucose, 5 g/l casein hydrolysate, 2.5 g/l yeast extract, 3.5 g/l K$_2$HPO$_4$, 1.5 g/l KH$_2$PO$_4$, 0.41 g/l MgCl$_2$.6H$_2$O, 10 mg/l FeSO$_4$.7H$_2$O, 2 mg/l MnSO$_4$.(4–6)H$_2$O, 0.9 mg/l ZnSO$_4$.7H$_2$O, 0.4 mg/l CuSO$_4$.5H$_2$O, 0.09 mg/l Na$_2$B$_4$O$_7$.10H$_2$O, 0.04 mg/l (NH$_4$)$_6$Mo$_7$O$_{24}$.4H$_2$O, 30 µg/l biotin, 2 mg/l thamine hydrochloride, and 135 g/l sodium succinate. To the cell suspension, lysozyme to a final concentration of 0.2 to 10 mg/ml, is added and the mixture is allowed to react at a temperature of 30 to 37° C. Protoplast formation proceeds with time and is monitored with an optical microscope. The period required for the conversion of most cells to protoplasts depends on the concentrations of the penicillin used for the lysozyme-sensitization and the amount of lysozyme used. The period is 3-24 hours under the conditions mentioned above.

Since protoplasts formed are destroyed under hypotonic conditions, the extent of the formation of protoplast is determined indirectly from the amount of normal cells surviving under hypotonic conditions. Generally, the ratio of surviving normal cells are kept below $10^{-4}$ per lysozyme-treated normal cell.

The protoplasts prepared as above have colony-forming (regenerating) ability on a suitable hypertonic agar medium. As a regeneration medium, a nutrient medium, a semi-synthetic medium or a synthetic medium containing various amino acids, which contains 0.3 to 0.8M sodium succinate and 0.5 to 6% polyvinyl pyrrolidone with a molecular weight of 10,000 or 40,000 is preferably used. Generally, a semi-synthetic medium RCGP (pH 7.2) wherein 3% polyvinyl pyrrolidone (molecular weight of 10,000) and 1.4% agar are added to the RCG medium is used. Regeneration is carried out at a temperature of 25° to 35° C. The cultivation time required for the regeneration of protoplasts depends upon the strain used but usually in 10 to 14 days formed colonies can be picked up. The efficiency of the regeneration of protoplasts on the RCGP medium also depends on the strain used, the concentrations of the penicillin added during the cultivation and the concentration of lysozyme used. The efficiency is generally $10^{-2}$–$10^{-4}$ cells per normal cells treated with lysozyme.

2. Transformation of the protoplast with a recombinant DNA

Introduction of a recombinant DNA into the protoplast is carried out by mixing the protoplast and the DNA in a hypertonic solution which protects the protoplast and by adding to the mixture polyethyleneglycol (PEG, average molecular weight: 1,540-6,000) or polyvinylalcohol (PVA, degree of polymerization: 500-1,500) and a divalent metal cation which stimulates the uptake of DNA. As a stabilizing agent in the hypertonic conditions, those generally used to protect protoplasts of other microorganisms such as sucrose and sodium succinate are also employed. PEG and PVA can be used at a final concentration of 5 to 60% and 1 to 20%, respectively. Divalent metal cations such as $Ca^{++}$, $Mg^{++}$, $Mn^{++}$, $Ba^{++}$ and $Sr^{++}$ are effectively used alone or in combination at a final concentration of 1 to 100 mM. Transformation is carried out satisfactorily at 0° to 25° C.

3. Regeneration of the protoplast to normal cells and selection of a transformant Regeneration of the protoplast transformed with a recombinant DNA is carried out in the same way as mentioned above by spreading the protoplast on a hypertonic agar medium such as RCGP medium containing sodium succinate and polyvinyl pyrrolidone and incubating at a temperature wherein normal cells can grow, generally 25° to 35° C. Transformants are obtained by selecting for the phenotype derived from donor DNAs. The selection may be carried out simultaneously with regeneration on a hypertonic agar medium or may be carried out on a hypotonic agar medium after non-selective reversion to normal cells on a hypertonic agar medium.

In the case of the lysozyme-sensitive strains described as the preferred host microorganisms in the present invention, the transformation may be carried out by the steps described in (1) to (3) except that the cultured cells are directly treated with lysozyme without prior treatment with penicillin. In that case, transformants are obtained at an efficiency of $10^{-4}$ to $10^{-6}$ per regenerated cell.

The phenotypic expression of the recombinant DNA is carried out by growing the transformant in a conventional nutrient medium. Appropriate reagents may be added to the medium according to the phenotypes expected from the genes on the recombinant DNA.

Recovery of useful substances such as amino acids produced by the method of the present invention is carried out in a conventional manner for recovering these substances from a culture liquor.

The present invention thus enables microorganisms of the genus Corynebacterium or Brevibacterium to produce amino acids, nucleic acids, vitamins, antibiotics, enzymes, peptides and proteins in higher yields or acquire a new ability to produce them. It has also become possible to enhance the metabolic activity of the microorganisms, increase rates of assimilation of substrates and endow the microorganisms with new metabolic activities and new assimilative activities of substrates.

Another feature of the present invention is the successful expression of foreign genes or foreign recombinant DNAs in microorganisms of the genus Corynebacterium or Brevibacterium. That is, the threonine operon and phosphoenolpyruvic acid carboxylase (PPC) gene of *Escherichia coli*, the $Km^R$ gene on the plasmid pUB110 which is expressible both in *Bacilus subtilis* and *Staphylococcus aureus* as described in Keggins K. M., et al., Proc. Natl. Acad. Sci., U.S.A. 75, 1423 (1978), the gene involved in the biosynthesis of lysine in *Corynebacterium glutamicum* and the anthranylate synthetase gene of *Brevibacterium flavum* have been expressed in microorganisms of the genus Corynebacterium as described in the examples below.

The genes mentioned above are inserted into the plasmid of *Corynebacterium glutamicum* by ligation without any special modification for expression. Moreover, these genes are expressed in *Corynebacterium glutamicum* when DNA fragments containing these genes are inserted into the plasmids of *Corynebacterium glutamicum* in either orientation. These facts show that *Corynebacterium glutamicum* can recognize precisely the transcription and translation signals of the introduced foreign genes to express them. Since all genes have homolgous base sequences for the precise initiation of transcription and translation, it can be easily deduced that *Corynebacterium glutamicum* can recognize initiation signals for transcription and translation of genes other than those exemplified to express them.

In spite of the high similarility in microbial characteristics, so called glutamic acid-producing microorganisms which produce glutamic acid in large amounts are classified into various species and genera such as Corynebacterium and Brevibacterium, probably because of their industrial importance. However, it has been pointed out that these microorganisms should be classified as belonging to one species based on the composition of amino acids in the cell wall and the base composition of DNAs. Recently, it has been reported that these microorganisms have 70 to 80% or more homology in DNA indicating that these microorganisms are closely related. See, e.g., Komatsu, Y.: Report of the Fermentative Research Institute, No. 55, 1 (1980), and Suzuki, K., Kaneko, T., and Komagata, K.: Int. J. Syst. Bacteriol., 31, 131 (1981).

In the present specification, the usefulness of the present invention is illustrated using derivatives of *Corynebacterium glutamicum* L-22 as host microorganisms because of the restrictions on experiments of recombinant DNA technology in Japan. However, in consideration of the facts mentioned above, it is apparent that the usefulness of the present invention is applicable to all the glutamic acid-producing microorganisms. In order to keep recombinant DNA molecules stable and express the DNA in these species, slight differences in such properties of the host microorganisms as homology in the DNA are negligible and it is sufficient for host microorganisms to allow the autonomous replication of plasmids and expression of genes on them. That these microorganisms have such ability is apparent from the fact that plasmid pCG4 which is isolated from *Corynebacterium glutamicum* 225-250 and having an $Sm^R/Spec^R$ gene can be replicated in microorganisms belonging to the genus Corynebacterium or Brevibacterium and the gene responsible for the resistance can be expressed. Therefore, the present invention is applicable to all the glutamic acid-producing microorganisms including those microorganisms belonging to the genus Corynebacterium or Brevibacterium as well as to *Corynebacterium glutamicum*.

Certain specific embodiments of the present invention are illustrated by the following representative examples.

EXAMPLE 1

Cloning of a gene involved in the biosynthesis of lysine derived from lysine-producing *Corynebacterium glutamicum* ATCC 21543 and production of lysine by the expression of the gene in *Corynebacterium glutamicum*:

1) Preparation of the chromosomal DNA of *Corynebacterium glutamicum* ATCC 21543 and the vector pCG11

The chromosomal DNA is extracted and isolated from the lysine-producing mutant strain, *Corynebacterium glutamicum* ATCC 21543 which was derived from *Corynebacterium glutamicum* ATCC 13032 and is resistant to a lysine analogue, S-(2-aminoethyl)-cysteine (referred to as AEC hereinafter) as follows:

A seed culture is inoculated into 400 ml of a semisynthetic medium SSM (pH 7.2) consisting of 20 g/l glucose 10 g/l $(NH_4)_2SO_4$, 3 g/l urea, 1 g/l yeast extract, 1 g/l $KH_2PO_4$, 0.4 g/l $MgCl_2.6H_2O$, 10 mg/l $FeSO_4.7H_2O$, 0.2 mg/l $MnSO_4.(4-6)H_2O$, 0.9 mg/l $ZnSO_4.7H_2O$, 0.4 mg/l $CuSO_4.5H_2O$, 0.09 mg/l $Na_2B_4O_7.10H_2O$, 0.04 mg/l $(NH_4)_6Mo_7O_{24}.4H_2O$, 30 µg/l biotin and 1 mg/l thiamine hydrochloride and containing 100 µg/ml threonine. Culturing is carried out with shaking at 30° C. The optical density (OD) at 660 nm is monitored with a Tokyo Koden Colorimeter and penicillin G is added at an OD value of 0.2 in a concentration of 0.5 unit/ml. Culturing is then continued to an OD value of about 0.6.

Cells are recovered from the culture broth and washed with TES buffer solution (pH 8.0) consisting of 0.03M tris(hydroxymethyl) aminomethane (referred to as Tris hereinafter), 0.005M EDTA, and 0.05M NaCl. The cells are suspended in a lysozyme solution (pH 8.0) consisting of 25% sucrose, 0.1M NaCl, 0.05M Tris and 0.8 mg/ml lysozyme to make 10 ml of a suspension which is allowed to react at 37° C. for 4 hours. High molecular chromosomal DNAs are isolated from the cells by the method of Saito et al., Biochim. Biophys. Acta, 72, 619 (1963).

Separately pCG11 used as a vector plasmid is isolated from *Corynebacterium glutamicum* LA 103/pCG11, ATCC 39022 which is a derivative of *Corynebacterium glutamicum* L-22 and harbors pCG11 as follows.

The strain is grown with shaking at 30° C. in 400 ml of NB medium (pH 7.2) consisting of 20 g/l powder bouillon and 5 g/l yeast extract to an OD value of about 0.7. Cells are recovered and washed with TES buffer solution. The cells are suspended in 10 ml of the aforementioned lysozyme solution and allowed to react at 37° C. for 2 hours. Then 2.4 ml of 5M NaCl, 0.6 ml of 0.5M EDTA (pH 8.5) and 4.4 ml of a solution consisting of 4% sodium lauryl sulfate and 0.7M NaCl are added successively. The mixture is stirred slowly and allowed to stand on an ice water bath for 15 hours. The whole lysate is put into a centrifugation tube and centrifuged at 4° C. under 69,400×g for 60 minutes. The supernatant fluid is recovered and 10% (by weight) polyethyleneglycol (PEG) 6,000 (product of Nakarai Kagaku Yakuhin Co.) is added. The mixture is stirred slowly to dissolve completely and then kept on an ice water bath. After 10 hours, the mixture is subjected to centrifugation at 1,500×g for 10 minutes to recover a pellet. The pellet is redissolved mildly in 5 ml of TES buffer solution. Then, 2.0 ml of 1.5 mg/ml ethidium bromide is added and cesium-chloride is added to adjust the density of the mixture to 1.580. The solution is subjected to centrifugation at 18° C. under 105,000×g for 48 hours. After the density gradient centrifugation, a covalently-closed circular DNA is detected by UV irradiation as a high density band located in the lower part of the centrifugation tube. The band is taken out from the side of the tube with an injector to obtain a fraction containing pCG11 DNA. To remove ethidium bromide, the fraction is treated five times with an equal amount of cesium chloride saturated isopropyl alcohol solution consisting of 90% by volume isopropyl alcohol and 10% TES buffer solution. Then, the residue is subjected to dialysis against TES buffer solution.

2) Cloning of the gene involved in the biosynthesis of lysine in *Corynebacterium glutamicum* ATCC 21543

In this step, 6 units of BglII (product of Takara Shuzo Co.) is added to 60 µl of a BglII reaction solution (pH 7.5) consisting of 10 mM Tris-hydrochloride, 7 mM $MgCl_2$, 60 mM NaCl and 7 mM 2-mercaptoethanol and containing 3 µg of pCG11 plasmid DNA prepared as above. The mixture is allowed to react at 37° C. for 60 minutes and heated at 65° C. for 10 minutes to stop the reaction.

Separately, 4 units of BamHI is added to 140 µl of a BamHI reaction solution (pH 8.0) consisting of 10 mM Tris-hydrochloride, 7 mM $MgCl_2$, 100 mM NaCl, 2 mM 2-mercaptoethanol and 0.01% bovine serum albumin and containing 8 µg of the chromosomal DNA of *Corynebacterium glutamicum* ATCC 21543. The mixture is allowed to react at 37° C. for 60 minutes and heated at 65° C. for 10 minutes to stop the reaction. Both digests are mixed and 40 µl of a T4 ligase buffer solution (pH 7.6) consisting of 660 mM Tris, 66 mM $MgCl_2$ and 100 mM dithiothreitol, 40 µl of 5 mM ATP, 0.3 µl of T4 ligase (product of Takara Shuzo Co., 1 unit/µl) and 120

μl of H₂O are added. The mixture is allowed to react at 12° C. for 16 hours. The reaction mixture is extracted twice with 400 μl of phenol saturated with the TES buffer solution and the extract is subjected to dialysis against the TES buffer solution to remove phenol.

*Corynebacterium glutamicum* LP4 which is derived from *Corynebacterium glutamicum* L-22 and is sensitive to AEC is transformed with the ligase reaction mixture. The transformation is carried out using the protoplast of LP4. The seed culture of LP4 is inoculated into NB medium and culturing is carried out with shaking at 30° C. Cells are harvested at an OD value of 0.6. The cells are suspended at about 10⁹ cells/ml in RCGP medium (pH 7.6) consisting of 5 g/l glucose, 5 g/l casamino acid, 2.5 g/l yeast extract, 3.5 g/l K₂HPO₄., 1.5 g/l KH₂PO₄, 0.41 g/l MgCl₂.6H₂O, 10 mg/l FeSO₄.7H₂O, 2 mg/l MnSO₄.(4–6)H₂O, 0.9 mg/l ZnSO₄.7H₂O, 0.04 mg/l (NH₄)₆Mo₇O₂₄.4H₂O, 30 μg/l biotin, 2 mg/l thiamine hydrochloride, 135 g/l sodium succinate and 30 g/l polyvinyl pyrrolidone with a molecular weight of 10,000 and containing 1 mg/ml lysozyme. The suspension is put in an L-tube and stirred slowly at 30° C. for 5 hours to obtain protoplasts.

Then, 0.5 ml of the protoplast suspension is put in a small test tube and subjected to centrifugation under 2,500×g for 5 minutes. The protoplasts are resuspended in 1 ml of TSMC buffer solution (pH 7.5) consisting of 10 mM magnesium chloride, 30 mM calcium chloride, 50 mM Tris and 400 mM sucrose and again subjected to centrifugation and washing. The washed protoplast is resuspended in 0.1 ml of TSMC buffer solution. 100 μl of a mixture (1:1 by volume) of a two-fold concentrated TSMC buffer solution and the ligated DNA mixture described above is added to the protoplast suspension. Then, 0.8 ml of a solution containing 20% PEG 6,000 in TSMC buffer solution is added to the mixture. After 3 minutes, 2 ml of RCGP medium (pH 7.2) is added and the mixture is subjected to centrifugation under 2,500×g for five minutes. The supernatant fluid is removed and the protoplasts are suspended in 1 ml of RCGP medium. Then, 0.2 ml of the suspension is spread on RCGP agar medium (pH 7.2) containing 400 μg/ml spectinomycin and 1.4% agar and culturing is carried out at 30° C. for 7 days.

All of the cells on the agar medium are scraped and washed with physiological saline solution. The cells are suspended in 1 ml of physiological saline solution and spread on a minimum agar medium MI (pH 7.2) consisting of 10 g/l glucose, 1 g/l NH₄H₂PO₄, 0.2 g/l KCl, 0.2 g/l MgSO₄.7H₂O, 10 mg/l FeSO₄.7H₂O, 0.2 mg/l MnSO₄.(4–6)H₂O, 0.9 mg/l ZnSO₄.7H₂O, 0.4 mg/l CuSO₄.5H₂O, 0.09 mg/l Na₂B₄O₇.10H₂O, 0.04 mg/l (NH₄)₆Mo₇O₂₄.4H₂O, 50 μg/l biotin, 2.5 mg/l p-aminobenzoic acid, 1 mg/l thiamine hydrochloride and 16 g/l agar and containing 2 mg/ml threonine, 2 mg/ml AEC and 12.5 μl/ml streptomycin. The agar medium is incubated at 30° C. for 3 days. The strains resistant to AEC, spectinomycin and streptomycin are obtained from the colonies formed.

Plasmids in the transformants are isolated by the same method as that used for the isolation of pCG11 mentioned above. 1 μg each of the plasmid DNAs is completely digested with EcoRI which cuts pCG11 and analyzed by agarose gel electrophoresis. The molecular weight of the plasmid is determined by summing up the molecular weights of fragments. The molecular weight of restricted fragments is determined by the standard curve plotted against electrophoretic distances of the fragments of known molecular weights which are obtained by digesting λphage DNA with HindIII on the same agarose gel electrophoresis. A plasmid pAec5 obtained from one of the transformants is a recombinant plasmid which has a molecular weight of 10.7 Kilo base pair (referred to as Kb hereinafter) and contains a 3.9 Kb DNA fragment at the BglII site in pCG11.

The protoplast of the LP4 strain is transformed with pAec5 DNA in the same manner as mentioned above. Transformants selected for spectinomycin-resistance have simultaneously acquired the AEC-resistance and have the same plasmid as pAec5 as judged by the EcoRI cleavage pattern. Therefore, it is certain that a gene controlling the resistance to AEC in *Corynebacterium glutamicum* ATCC 21543 was cloned in the plasmid pAec5. A strain having pAec5 has been deposited with the American Type Culture Collection, U.S.A. as *Corynebacterium glutamicum* K17 ATCC 39032 on Dec. 21, 1981.

3) Production of lysine by the strain having pAec5

The LP4 strain derived from *Corynebacterium glutamicum* L-22 and the LP4 strain harbouring the plasmid pAec5 are tested for L-lysine production (ATCC 39032). A loopful of cells cultured on the NB agar medium is inoculated in 5 ml of a production medium P1 (pH 7.2) consisting of 100 g/l glucose, 24.5 g/l (NH₄)₂SO₄, 1 g/l KH₂PO₄, 0.4 g/l MgSO₄.7H₂O, 10 mg/l FeSO₄.7H₂O, 10 mg/l MnSO₄.(4–6)H₂O, 50 μg/l biotin, 200 μg/l thiamine hydrochloride, 500 μg/l calcium pantothenate, 500 μg/l nicotinic acid, 10 g/l soybean hydrolyzate and 30 g/l calcium carbonate in a test tube. Culturing is carried out with shaking at 30° C. for 75 hours. The amount of L-lysine formed is determined by a colorimetric method using an acid-Cu ninhydrin reaction. The results are shown in Table 1.

TABLE 1

| Strain | Amount of L-lysine (mg/ml) |
|---|---|
| LP-4 | 0 |
| LP-4/pAec5 | 7.2 |

EXAMPLE 2

Cloning of genes involved in the biosynthesis of L-threonine and production of L-threonine in *Corynebacterium glutamicum* through the expression of the cloned genes:

1) Cloning of a DNA fragment containing an *Escherichia coli* threonine operon and introduction thereof in *Corynebacterium glutamicum*

Cloning is carried out using the host-vector system of *Escherichia coli*. Plasmid pGA22 used as a vector is isolated from a derivative of *Escherichia coli* K-12 by the method of An, et al., J. Bacteriol., 140, 400 (1979) who prepared the plasmid. A high molecular chromosomal DNA used as a donor DNA is isolated from the cultured cells of *Escherichia coli* K-12 (ATCC 23740) by the phenol-extraction method of Smith, Method In Enzymology, 12, part A, 545 (1967). Then, 0.4 unit of HindIII (product of Takara Shuzo Co., 6 units/μl) is added to 60 μl of a HindIII reaction solution (pH 7.5) consisting of 10 mM Tris-HCl, 7 mM MgCl₂ and 60 mM NaCl and containing 4 μg of pGA22 plasmid DNA. The mixture is allowed to react at 37° C. for 30 minutes and heated at 65° C. for 10 minutes to stop the reaction.

pGA22 plasmid DNA is digested with HindIII under the same conditions as above, and subjected to agarose gel electrophoresis to confirm that only one of the two HindIII cleavage sites of pGA22 is cleaved.

Separately, 4 units of HindIII is added to 140 μl of the HindIII reaction solution containing 8 μg of the chromosomal DNA. The mixture is allowed to react at 37° C. for 60 minutes and heated at 65° C. for 10 minutes to stop the reaction.

Both digests are mixed and to the mixture, 40 μl of T4 ligase buffer solution, 40 μl of ATP (5 mM), 0.3 μl of T4 ligase and 120 μl of H$_2$O are added. The ligation is carried out at 12° C. for 16 hours. The reaction mixture is extracted twice with 400 μl of phenol saturated with TES buffer solution and subjected to dialysis against TES buffer solution to remove phenol.

The ligase reaction mixture is used to transform *Escherichia coli* GT-3 described in J. Bacteriol. 117, 133–143 (1974) which is a derivative strain of *Escherichia coli* K-12 and requires homoserine and diaminopimelic acid. Competent cells of the GT-3 strain which can take up DNAs are prepared according to the method of Dagert et al., Gene, 6, 23 (1979). That is, the strain is inoculated in 50 ml of L-medium (pH 7.2) consisting of 10 g/l Bactotryptone and 5 g/l yeast extract and containing 100 μg/ml diaminopimelic acid. Culturing is carried out at 37° C. to an OD value of 0.6. The culture liquor is cooled with ice water for 10 minutes and cells are recovered by centrifugation. The cells are suspended in 20 ml of cooled 0.1M calcium chloride. The suspension is allowed to stand at 0° C. for 20 minutes and subjected to centrifugation to recover the cells. The cells are suspended in 0.5 ml of 0.1M calcium chloride and allowed to stand at 0° C. for 18 hours.

200 μl of the ligase reaction mixture described above is added to 400 μl of the cell suspension treated with calcium chloride. The mixture is allowed to stand at 0° C. for 10 minutes and heated at 37° C. for 5 minutes. Then, 9 ml of L-medium is added and the mixture is cultured with shaking at 37° C. for 2 hours. Cells are recovered by centrifugation and washed with physiological saline solution twice. The cells are spread on M9 minimum agar medium (pH 7.2) consisting of 2 g/l glucose, 1 g/l NH$_4$Cl, 6 g/l Na$_2$HPO$_4$, 3 g/l KH$_2$PO$_4$, 0.1 g/l MgSO$_4$.7H$_2$O, 15 mg/l CaCl$_2$.2H$_2$O, 4 mg/l thiamine hydrochloride and 15 g/l agar and containing 12.5 μg/ml kanamycin. Culturing is carried out at 37° C. for 3 days. It is confirmed that the only colony formed can also grow on L-agar medium containing 25 μg/ml ampicillin, 25 μg/ml chloramphenicol or 25 μg/ml of kanamycin.

A plasmid DNA is isolated from cultured cells of the transformant by the same method as in the isolation of pGA22 in step (1) above. The plasmid DNA is digested with restriction endonucleases and analyzed by agarose gel electrophoresis. The plasmid DNA has the structure illustrated as pGH2 in FIG. 1. Since the DNA fragment inserted in pGA22 has the same cleavage sites for restriction endonucleases as the cloned DNA fragment containing the *Echerichia coli* operon as reported by Cossart, P. et al., Molec. Gen. Genet., 175, 39 (1979), it is clear that pGH2 contains the *Escherichia coli* threonine operon.

Next, a recombinant of pCG11 and pGH2 is prepared as follows. pCG11 and pGH2 are completely digested with BglII and BamHI respectively. Both digests containing 2 μg each of plasmid DNAs are mixed. Then, 40 μl of T4 ligase buffer solution, 40 μl of ATP (5 mM), 0.2 μl of T4 ligase and 120 μl of H$_2$O are added to the mixture (200 μl). Reaction is carried out at 12° C. for 16 hours. The reaction mixture is extracted twice with 400 μl of phenol saturated with TES buffer solution and subjected to dialysis against TES buffer solution to remove phenol.

Protoplasts of *Corynebacterium glutamicum* LA 201 which is a derivative strain of the LA 103 strain and requires homoserine and leucine are transformed using, as a donor DNA, 100 μl of a mixture of a two-fold concentrated TSMC buffer solution and the ligase reaction mixture mentioned above (1:1) in the same manner as in Example 1 (1). The transformants are spread on the RCGP agar medium and culturing is carried out at 30° C. for 6 days to regenerate the tranformants. Cells grown over the whole surface of the agar medium are scraped, washed with physiological saline solution and subjected to centrifugation. The cells are again spread on the minimum agar medium M1 containing 50 μg/ml leucine and culturing is carried out at 30° C. for 3 days. Colonies formed are subjected to selection on NB agar medium containing 12.5 μg/ml kanamycin or 100 μg/ml spectinomycin. The plasmids are isolated from the transformants by ethidium bromide-cesium chloride density gradient centrifugation described in Example 1 (1).

Figure 3:
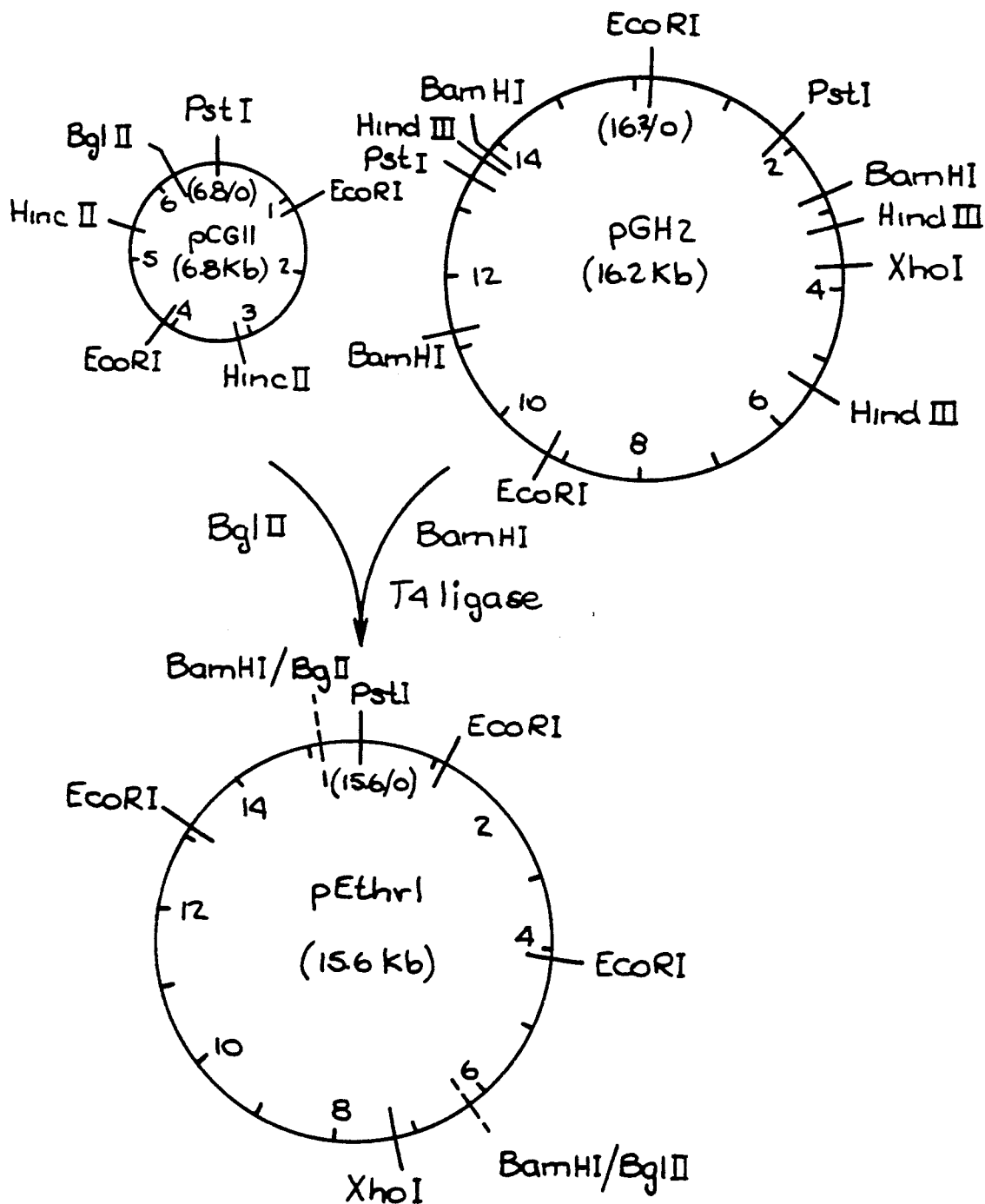
FIG. 3 is a cleavage map of the plasmid pEthr1 and an illustration of the process for construction thereof.

Then, 0.5 μg each of these plasmid DNAs is digested or double-digested with restriction endonucleases and the fragments are analyzed by agarose gel electrophoresis to determine the molecular weight and cleavage sites for various restriction endonucleases. One plasmid thus obtained is named pEthr1 and its structure characterized by the cleavage sites for PstI, EcoRI and XhoI is illustrated in FIG. 3. By characterization of structure using various restriction endonucleases it is confirmed that pEthr1 has the structure wherein a BamHI fragment containing pGH2 threonine operon is combined with pCG11.

*Corynebacterium glutamicum* LA 103 is transformed with pEthr1 DNA as mentioned above. The non-requirement for homoserine is introduced into transformants simultaneously with Km$^R$ and Spec$^R$. The transformants have the same plasmid as pEthr1 characterized by the cleavage pattern by various restriction endonucleases. The reversion of homoserine-requirement of the LA 103 strain which lacks homoserine dehydrogenase to homoserine-non-requirement results from the expression of the homoserine dehydrogenase on the threonine operon of *Escherichia coli*.

2. Construction of the strain carrying pEthr1.

*Corynebacterium glutamicum* LA-106 (met$^-$, AEC$^R$, α-amino-β-hydroxy varelic acid$^R$) is a threonine-producing derivative of *Corynebacterium glutamicum* L-22. The protoplasts of the LA-106 strain is used to introduce pEthr1 into the LA-106 strain.

The protoplast is prepared by culturing the LA-106 strain in a semisynthetic medium SSM containing 100 μg/ml methionine to an OD value of about 0.6 and treating the cells as in Example 1 (2). Transformation is carried out in the same way as in Example 1 (2) and transformants are selected on a RCGP agar medium containing 400 μg/ml spectinomycin. Plasmid pEthr1 has been deposited with the American Type Culture Collection, U.S.A. as *Corynebacterium glutamicum* K19 ATCC 39034 on Dec. 21, 1981.

3. Production of threonine by the strain carrying pEthr1.

The LA-106 strain and the strain ATCC 39034 carrying pEthr1 prepared as above are tested for threonine production. One loopful of cells grown on NB agar medium is inoculated in 5 ml of production medium P2 (pH 7.2) consisting of 100 g/l glucose, 20 g/l (NH$_4$)$_2$SO$_4$, 0.5 g/l KH$_2$PO$_4$, 0.5 g/l K$_2$HPO$_4$, 1 g/l MgSO$_4$.7H$_2$O, 10 mg/l FeSO$_4$.7H$_2$O, 10 mg/l MnSO$_4$.(4-6)H$_2$O, 100 µg/l biotin, 20 g/l calcium carbonate and 100 mg/l methionine in a test tube. Culturing is carried out with shaking at 30° C. for 75 hours. The culture broth is filtered and the filtrate is subjected to paper chromathography and ninhydrin color reaction. The color is measured with a colorimeter to determine the amount of L-threonine formed.

TABLE 2

| Strain | Amount of L-threonine (mg/ml) |
| --- | --- |
| LA-106 | 6.1 |
| LA-106/pEthr1 | 13.4 |

EXAMPLE 3

Production of glutamic acid by a *Corynebacterium glutamicum* strain carrying a recombinant plasmid containing phosphoenolpyruvic acid carboxylase (PPC) gene of *Escherichia coli*:

(1) Cloning of a DNA fragment containing PEP carboxylase gene which is involved in the biosynthesis of glutamic acid and can transform Glu$^-$ *Escherichia coli* to Glu$^+$, and introduction of the cloned DNA into *Corynebacterium glutamicum*.

Cloning is carried out using the host-vector system of *Escherichia coli*. pBR322 used as a vector is isolated from the cultured cells of a derivative of *Escherichia coli* K-12 in the same way as in the preparation of pGA22 in Example 1 (1). A high molecular chromosomal DNA prepared from *Escherichia coli* K-12 (ATCC 23740) in Example 2 (1) is used as a donor DNA.

10 units of Sa;lI (product of Takara Shuzo Cpo.) is added to 200 µl of a SalI reaction solution (pH 7.5 consisting of 10 mM Tris-hydrochloride, 7 mM MgCl$_2$, 100 mM NaCl, 7 mM 2-mercaptoethanol and 0.01% bovine serum albumin) containing 3 µg of pBR322 and 9 µg of the chromosomal DNA. The mixture is allowed to react at 37° C. for 60 minutes and heated at 65° C. for 10 minutes to stop the reaction. Then, 40 µl of the T4 ligase buffer solution, 40 µl of 5 mM ATP, 0.4 µl of T4 ligase and 120 µl of water are added to the digest and reaction is carried out at 12° C. for 16 hours. The mixture is extracted twice with 400 µl of phenol saturated with TES buffer solution and the extract is subjected to dialysis against TES buffer solution to remove phenol.

The ligase reaction mixture is used to transform *Escherichia coli* PPC2 described in Glansdorff, N., Genetics 51, 167 (1965) (arg$^-$, thr$^-$, leu$^-$, his$^-$, Thi$^-$, PPC$^-$, ST$^R$) and which is a derivative of *Escherichia coli* K-12. Competent cells of the PPC2 strain are obtained by culturing the strain in L-medium containing 2 mg/ml glutamic acid as in the preparation of the competent cells of the GT-3 strain in Example 2 (1). Transformation is carried out using 200 µl of the ligase reaction mixture mentioned above as in Example 2 (1). Then, 9 ml of L-medium is added and culturing is carried out with shaking at 37° C. for 2 hours for the expression of the gene. Cells are harvested and washed with physiological saline solution and centrifuged twice. The cells are spread on M9 minimum agar medium containing 50 µg/ml each of arginine, threonine, leucine and histidine and incubated at 37° C. for 3 days. Colonies formed are replicated on L-agar medium containing 25 µg/ml ampicillin or 25 µg/ml tetracycline. The agar plate is incubated at 37° C. for 24 hours. Colonies resistant to ampicillin and sensitive to tetracycline are selected as transformants.

Plasmid DNAs are isolated form the cultured cells of the transformants by the same method as mentioned above. Plasmid pPC1 obtained from one of the transformants is analyzed by digestion with restriction endonucleases and agarose gel electrophoresis. As a result, pPC1 is found to be a recombinant plasmid of 8.8 Kb wherein a DNA fragment of 4.4 Kb is inserted into the SalI cleavage site of pBR322.

The PPC2 strain is transformed with the pPC1 plasmid in the same way as mentioned above. The transformants selected for resistance to ampicillin are all glutamic acid-non-requiring strains and have the plasmid with the same structure as that of pPC1 characterized by the cleavage pattern. This show that the PPC gene of *Escherichia coli* is cloned on the pPC1 plasmid.

In order to introduce the cloned PPC gene into *Corynebacterium glutamicum*, a recombinant plasmid of pCG11 and pPC1 is obtained from *Escherichia coli* PPC2 as follows. 4 units of PstI (product of Takara Shuzo Co.) is added to 200 µl of a PstI reaction buffer solution (pH 7.5), consisting of 20 mM Tris-hydrochloride, 10 mM MgCl$_2$, 50 mM (NH$_4$)$_2$SO$_4$ and 0.01% bovine serum albumin and containing 2 µg each of pCG11 and pPC plasmid DNAs. The mixture is allowed to react at 30° C. for 60 minutes and heated at 65° C. for 10 minutes to stop the reaction. Then, 40 µl of the T4 ligase buffer solution, 40 µl of 5 mM ATP, 0.2 µl of T4 ligase and 120 µl of water are added to the reaction mixture and the mixture is allowed to react at 12° C. for 16 hours. The reaction mixture is extracted with phenol and subjected to dialysis to remove phenol in the same way as mentioned above. The PPC2 strain is transformed with 100 µl of the ligase reaction mixture as mentioned above. Plasmids are isolated from the colonies formed and subjected to agarose gel electrophoresis to determine the sizes of the plasmids as mentioned above.

Strains having plasmids of about 15 to 16 Kb are selected and the PPC2 strain is again transformed with them to confirm the presence of the PPC gene. The plasmid pEppc1 obtained from one of the above transformants is analyzed by digestion with restriction endonucleases and agarose gel electrophoresis. As a result, pEppc1 was found to be a recombinant plasmid of 15.6 Kb wherein pCG11 and pPC1 are joined at the PstI site of both plasmids. The LP-4 strain derived from *Corynebacterium glutamicum* L-22 is transformed using the pEppc1 plasmid DNA thus prepared from *Escherichia coli*. Transformation is carried out in the same way as in Example 1 (2). Transformants are obtained from the colonies formed on RCGP agar medium containing 400 µg/ml spectinomycin. The plasmids isolated from the transformants are examined by digestion with SalI or PstI or by double digestion with SalI and PstI and agarose gel electrophoresis, whereby the presence of pEppc1 is confirmed.

A microorganism containing plasmid pEppc1, *Corynebacterium glutamicum* K-18, has been deposited with the American Type Culture Collection, U.S.A. under accession number ATCC 39033 on Dec. 21, 1981.

2. Production of glutamic acid by the strain carrying pEppc1.

The LP4 strain derived from *Corynebacterium glutamicum* L-22 and the strain carrying pEppc1, ATCC 39033 are tested for glutamic acid production. Cells grown on NB agar medium are scraped and washed with physiological saline solution. The cells are inoculated in 5 ml of a production medium P3 (pH 7.2) consisting of 50 g/l glucose, 3 g/l $(NH_4)_2SO_4$, 3 g/l urea, 0.5 g/l $KH_2PO_4$, 0.5 g/l $K_2HPO_4$, 0.5 g/l $MgSO_4.7H_2O$, 10 mg/l $FeSO_4.7H_2O$, 10 mg/l $MnSO_4.(4-6)H_2O$, 3 µg/l biotin, 500 µg/l thiamine hydrochloride and 10 mg/l phenol red in a test tube and cultured with shaking at 30° C. During culturing, 0.2 ml of 20% urea solution is added three times and culturing is continued for 40 hours. The culture broth is filtered and the filtrate is subjected to paper chromatography. After ninhydrin color reaction, the amount of L-glutamic acid is determined colorimetrically. The results are shown in Table 3.

TABLE 3

| Strain | L-glutamic acid (mg/ml) |
| --- | --- |
| LP-4 | 10.1 |
| LP-4/pEppc1 | 15.8 |

EXAMPLE 4

Cloning and expression of the anthranilic acid synthetase gene of *Brevibacterium flavum* ATCC 14067 in *Corynebacterium glutamicum*:

The chromosomal DNA of *Brevibacterium flavum* ATCC 14067 is prepared by the same method as in Example 1 (1). Plasmid pCE53 used as a vector is isolated from cultured cells of *Corynebacterium glutamicum* L-22 in the same way as in the isolation of pCG11 in Example 1 (1). Plasmid pCE53 is a recombinant plasmid wherein plasmid pCG1 is combined with plasmid pGA22 of *Escherichia coli* described by An, G. et. al., J. Bacteriol 140, 400 (1979). More specifically, the only BglII cleavage site on pCG1 and one of the two BamHI sites of pGA22, which cuts out the $Tc^R$ gene, are ligated by taking advantage of the same cohesive ends formed by both restriction enzymes. pCE53 has selective markers such as $Km^R$ derived from pGA22 and has only one cleavage site for SalI.

10 units of SalI is added to 200 µl of the SalI reaction solution containing 3 µg of pCE53 plasmid DNA prepared as above and 9 µg of the chromosomal DNA. The mixture is allowed to react at 37° C. for 60 minutes and heated at 65° C. for 10 minutes to stop the reaction. Then, 40 µl of the T4 ligase buffer solution, 40 µl of 5 mM ATP, 0.4 µl of T4 ligase and 120 µl of $H_2O$ are added to the digest. The mixture is allowed to react at 12° C. for 16 hours. The reaction mixture is extracted with 400 µl of phenol saturated with TES buffer solution and the extract is subjected to dialysis against TES buffer solution to remove phenol.

The ligase reaction mixture is used for the following transformation. The LA 105 strain which is a mutant requiring anthranilic acid due to the lack of the anthranilic acid synthetase gene and derived from *Corynebacterium glutamicum* L-22 is used as a host microorganism. The mutant requiring anthranilic acid is obtained by conventional mutagenesis as a strain which can not grow on M1 agar medium but can propagate on the M1 agar medium containing 30 µg/ml anthranilic acid. Preparation of the protoplasts of the LA 105 strain and transformation of the protoplasts are carried out in the same way as in Example 1 (2) except that the NB medium contains 100 µg/ml anthranilic acid. Transformants are selected as colonies grown on RCGP agar medium containing 200 µg/ml kanamycin. Transformants are further selected for anthranilic acid+ phenotype on M1 agar medium.

Plasmids DNAs are isolated from the cultured cells of these transformants in the same way as mentioned above. The plasmid pTrp2-3, recovered from one of the transformants, is analyzed by digestion with various restriction endonucleases and agarose gel electrophoresis. As a result, the plasmid pTrp2-3 is found to be a plasmid wherein a 7.1 Kb SalI DNA fragment is inserted into the only SalI cleavage site of pCE53.

The LA 105 strain is again transformed with pTrp2-3 in the same way as mentioned above. The colonies grown on RCGP agar medium containing 100 µg/ml tryptophan and 400 µg/ml kanamycin do not require anthranilic acid for growth and they have the same plasmid as pTrp2-3 characterized by the cleavage pattern by SalI.

The result shows that the gene coding for anthranilic acid synthetase of *Brevibacterium flavum* ATCC 14067 is present in the cloned 7.1 Kb SalI DNA fragment and expressed in *Corynebacterium glutamicum* LA 105.

A microorganism containing pTrp2-3, *Corynebacterium glutamicum* K-20, has been deposited with the American Type Culture Collection, U.S.A. under accession number ATCC 39035.

Plasmid pTrp4-3 having a gene coding for anthranilic acid synthetase of *Brevibacterium flavum* ATCC 14067 is obtained using plasmid pCE52 by the same method as mentioned above.

pCE52 is also obtained by the in vitro recombination between plasmid pCG1 of *Corynebacterium glutamicum* and plasmid pGA22 of *Escherichia coli* Specifically, plasmid pCE52 is constructed by inserting the linearized pGA22 cut at the BamHI site in the gene for tetracycline resistance into the unique BglII site of pCG1 by taking advantage of the same cohesive ends formed by both restriction enzymes. pCE52 has selection markers such as a gene for kanamycin resistance derived from pGA22 and has a unique cleavage site for the restriction enzyme SalI.

pCE52 is isolated from cultured cells of *Corynebacterium glutamicum* L-22 containing pCE52 by the same method as in the isolation of pCG11 in Example 1 (1).

*Corynebacterium glutamicum* LAR-1 (FERM P-6908) which is capable of producing tryptophan is transformed with pTrp4-3 by the same method as mentioned above. The resultant transformant has been deposited with the American Type Culture Collection, U.S.A. as *Corynebacterium glutamicum* K31, ATCC 39280.

*Corynebacterium glutamicum* K20, ATCC 39035 containing pTrp2-3 and *Corynebacterium glutamicum* K31, ATCC 39280 containing pTrp4-3 are tested for L-tryptophan production in the following manner.

The two strains are cultured with shaking in NB aqueous medium at 30° C. for 16 hours. Then, 0.5 ml of the resultant culture is inoculated in 5 ml of a production medium P4 (pH 7.2) consisting of 100 g/l molasses, 20 g/l $(NH_4)_2SO_4$, 0.5 g/l $KH_2PO_4$, 0.5 g/l $K_2HPO_4$, 0.25 g/l $MgSO_4.7H_2O$ and 20 g/l $CaCO_3$ in a test tube and culturing is carried out with shaking at 30° C. for 96 hours.

After completion of culturing, the culture filtrate is subjected to paper chromatography and colorimetric determination with ninhydrin to measure the amount of L-tryptophan produced.

As controls, the LA-105 strain and the LAR-1 strain are tested in the same manner. The results are shown in Table 4.

TABLE 4

| Strain | L-tryptophan (mg/ml) |
| --- | --- |
| LA-105 | — |
| LA-105/pTrp2-3 (K20, ATCC 39035) | 0.34 |
| LAR-1 | 0.48 |
| LAR-1/pTrp4-3 (K31, ATCC 39280) | 1.12 |

EXAMPLE 5

Cloning of a gene responsible for the biosynthesis of L-histidine of *Corynebacterium glutamicum* C156 and production of L-histidine by the expression of the gene in *Corynebacterium glutamicum, Corynebacterium herculis, Brevibacterium flavum* and *Brevibacterium lactofermentum*:

1) Preparation of a chromosomal DNA of *Corynebacterium glutamicum* C156 and plasmid pCG11.

A chromosomal DNA is prepared by the same method as in Example 1 (1) from *Corynebacterium glutamicum* C156 (FERM P-6910) which is resistant to 1,2,4-triazole-3-alanine and capable of producing histidine.

Separately, pCG11, to be used as a vector plasmid, is isolated from the LA103 strain derived from *Corynebacterium glutamicum* L-22 and containing pCG11, i.e. LA103/pCG11 (ATCC 39022) by the same method as in Example 1 (1).

2) Cloning of a gene responsible for the biosynthesis of histidine of *Corynebacterium glutamicum* C156.

In this step, 10 units of BglII (product of Takara Shuzo Co.) is added to 200 μl of a reaction solution for the restriction enzyme BglII consisting of 10 mM Tris (pH 7.5), 7 mM MgCl$_2$, 60 mM NaCl and 7 mM 2-mercaptoethanol and containing 3 μg of plasmid pCG11 DNA prepared as above and 9 μg of the chromosomal DNA obtained as above. The mixture is allowed to react at 37° C. for 60 minutes and the reaction is stopped by heating at 65° C. for 10 minutes. To the mixed digest, 40 μl of a buffer solution for T4 ligase (pH 7.6) consisting of 200 mM Tris, 66 mM MgCl$_2$ and 100 mM dithiothreitol, 40 μl of 5 mM ATP solution, 0.3 μl of T4 ligase (product of Takara Shuzo Co., 1 unit/μl) and 120 μl of water are added. Reaction is carried out at 12° C. for 16 hours.

The T4 ligase reaction mixture is used for the transformation of *Corynebacterium glutamicum* LH33 which requires histidine for growth and is sensitive to lysozyme.

The transformation is carried out using protoplasts of the LH33 strain. The protoplasts are prepared by the same method as in Example 1 (2). Then, 0.5 ml of a protoplast suspension is put in a small test tube and subjected to centrifugation at 2,500×g for 5 minutes. The protoplasts are resuspended in 1 ml of TSMC buffer solution (pH 7.5) consisting of 10 mM magnesium chloride, 30 mM calcium chloride, 50 mM Tris and 400 mM sucrose and subjected to centrifugation and washing. The resultant precipitate is resuspended in 0.1 ml of TSMC buffer solution. Then, 100 μl of a mixture of two-fold concentrated TSMC buffer solution and the ligated DNA mixture mentioned above (1:1) is added to the suspension, followed by addition of 0.8 ml of TSMC buffer solution containing 20% PEG6,000. After three minutes, 2 ml of RCGP medium (pH 7.2) is added and the mixture is subjected to centrifugation at 2,500×g for 5 minutes to remove supernatant fluid. The precipitated protoplasts are suspended in 1 ml of RCGP medium and 0.2 ml of the suspension is spread on RCGP agar medium (pH 7.2) which contains 400 μg/ml spectinomycin and 1.4% agar. Culturing is carried out at 30° C. for 7 days.

Spectinomycin-resistant colonies grown on the selection medium are collected and washed with physiological saline solution and centrifuged twice. The precipitate is spread on a minimum agar medium M1 containing 100 μg/ml spectinomycin and culturing is carried out at 30° C. for 2 days to select transformants which are resistant to spectinomycin and do not require histidine for growth.

A plasmid is isolated from one of these transformants by ethidium bromide-cesium chloride density gradient centrifugation as in Example 1 (1). The plasmid is digested and double-digested with various restriction enzymes and the resulting DNA fragments are analyzed by agarose gel electrophoresis to determine the restriction pattern of the plasmid DNA, which is named pPH8. pPH8 has a structure wherein a DNA fragment of about 10.6 Kb is inserted in the BglII site of pCG11.

pPH8 DNA is used for the retransformation of the H33 strain (FERM P-6909) which is the parent strain of the LH33 strain and requires histidine for growth and is resistant to lysozyme. None of the spectinomycin-resistant transformants obtained require histidine for growth, indicating that genes encoding enzymes involved in the biosynthesis of histidine of the histidine-producing C156 strain is cloned in the plasmid.

Cloning of genes encoding enzymes involved in the biosynthesis of histidine can also be carried out using the H33 strain as a host.

3) Production of L-histidine by *Corynebacterium glutamicum* carrying pPH8

*Corynebacterium glutamicum* LA-103 (FERM P-5947, ATCC 31866) is transformed with pPH8 DNA and a transformant resistant to spectinomycin is selected on an RCGP agar medium containing 400 μg/ml spectinomycin. The transformant is purified and the plasmid is isolated and analyzed to determine the structure, whereby the plasmid is confirmed to have the same structure as that of pPH8.

*Corynebacterium glutamicum* LA103/pPH8 containing pPH8 has been deposited with the American Type Culture Collection, U.S.A. as *Corynebacterium glutamicum* K32, ATCC 39281.

*Corynebacterium glutamicum* LA103/pCG11 (ATCC 39022) and *Corynebacterium glutamicum* LA103/pPH8 (ATCC 39281) are tested for L-histidine production in the following manner.

The two strains are cultured in NB agar medium at 30° C. overnight and a loopful of the cells is inoculated in 5 ml of a production medium P5 (adjusted to pH 7.4 with ammonia) consisting of 12% molasses (as sugar), 0.2% KH$_2$PO$_4$, 0.1% K$_2$HPO$_4$, 0.05% MgSO$_4$.7H$_2$O, 0.25% NaCl, 2.3% (NH$_4$)$_2$SO$_4$, 0.2% urea and 2% CaCO$_3$ and containing 200 μg/ml arginine and 200 μg/ml methionine. Culturing is carried out at 30° C. for 75 hours and the amount of L-histidine in the medium is determined by the colorimetric method using sulfanilic acid (Pauly) reagent of H. Pauly, Hoppe-Seylers: Z. Physiolo. Chem., 42, 508 (1904), ibid. 94, 284 (1915). The results are shown in Table 5.

TABLE 5

| Strain | L-histidine (mg/ml) |
|---|---|
| LA-103/pCG11 | 0 |
| LA-103/pPH8 (K32) | 2.6 |

4) Production of L-histidine by *Corynebacterium herculis*, *Brevibacterium flavum* and *Brevibacterium glutamicum* carrying pPH8.

*Corynebacterium herculis* ATCC 13868, *Brevibacterium flavum* ATCC 14067 and *Brevibacterium lactofermentum* ATCC 13869 are transformed with pPH8.

Each strain is grown in SSM medium and 0.3 units/ml penicillin G is added at an OD$_{660}$ value of 0.2. Culturing is continued and cells are collected at an OD$_{660}$ value of 0.6. The cells are treated in RCGP medium containing 1 mg/ml lysozyme by the same method as mentioned above to form protoplasts. Transformation is carried out using pPH8 as mentioned above and transformants are selected as colonies grown on RCGP agar medium containing 400 μg/ml spectinomycin.

The transformants resistant to spectinomycin are purified and plasmid DNAs are prepared from the cultured cells thereof according to the method of Japanese Published Unexamined Patent Application Nos. 183799/82 and 134500/82. By analysis of the restriction enzyme cleavage pattern it is confirmed that the plasmids have the same structure as that of pPH8, and establishes that plasmid pPH8 derived from plasmid pCG11 is replicable in *Corynebacterium herculis*, *Brevibacterium flavum* and *Brevibacterium lactofermentum* and that plasmid pCG11 is broadly applicable to these bacteria.

Strains containing pPH8, *Corynebacterium herculis* K33, *Brevibacterium flavum* K34 and *Brevibacterium lactofermentum* K35 have been deposited with the American Type Culture Collection, U.S.A. as ATCC 39282, 39283 and 39284 respectively.

These strains are tested for L-histidine production in the following manner. Strains harboring plasmid pPH8 and the parent strains thereof are cultured on NB agar medium at 30° C. overnight and a loopful of the cells is inoculated in 5 ml of P5 medium. Culturing is carried out with shaking at 30° C. for 75 hours and the amount of L-histidine in the medium is determined colorimetrically by the above-mentioned method of Pauly. The results are shown in Table 6.

TABLE 6

| Strain | L-histidine (mg/ml) |
|---|---|
| ATCC 13868 | 0 |
| ATCC 13868/pPH8 (K33, ATCC 39282) | 2.4 |
| ATCC 14067 | 0 |
| ATCC 14067/pPH8 (K34, ATCC 39283) | 3.0 |
| ATCC 13869 | 0 |
| ATCC 13869/pPH8 (K35, ATCC 39284) | 2.0 |

The above results show that genes responsible for the production of histidine in *Corynebacterium glutamicum* are expressed in other bacteria such as *Corynebacterium herculis*, *Brevibacterium flavum* and *Brevibacterium lactofermentum* and contribute to the production of histidine.

Plasmid pTrp4-3 having a gene coding for anthranilic acid synthetase of *Brevibacterium flavum* ATCC 14067 is obtained using plasmid pCE52 by the same method as mentioned above.

pCE52 is also obtained by the in vitro recombination between plasmid pCG1 of *Corynebacterium glutamicum* and plasmid pGA22 of *Escherichia coli*. Specifically, plasmid pCE52 is constructed by inserting the linearized pGA22 cut at the BamHI site in the gene for tetracycline resistance into the unique BglII site of pCG1 by taking advantage of the same cohesive ends formed by both restriction enzymes. pCE52 has selection markers such as a gene for kanamycin resistance derived from pGA22 and has a unique cleavage site for the restriction enzyme SalI.

pCE52 is isolated from cultured cells of *Corynebacterium glutamicum* L-22 containing pCE52 by the same method as in the isolation of pCG11 in Example 1 (1).

*Corynebacterium glutamicum* LAR-1 (FERM P-6908) which is capable of producing tryptophan is transformed with pTrp4-3 by the same method as mentioned above. The resultant transformant has been deposited with the American Type Culture Collection, U.S.A. as *Corynebacterium glutamicum* K31, ATCC 39280.

*Corynebacterium glutamicum* K20, ATCC 39035 containing pTrp2-3 and *Corynebacterium glutamicum* K31, ATCC 39280 containing pTrp4-3 are tested for L-tryptophan production in the following manner.

The two strains are cultured with shaking in NB medium at 30° C. for 16 hours. Then, 0.5 ml of the resultant culture is inoculated in 5 ml of a production medium P4 (pH 7.2) consisting of 100 g/l molasses, 20 g/l (NH$_4$)$_2$SO$_4$, 0.5 g/l KH$_2$PO$_4$, 0.5 g/l K$_2$HPO$_4$, 0.25 g/l MgSO$_4$.7H$_2$O and 20 g/l CaCO$_3$ in a test tube and culturing is carried out with shaking at 30° C. for 96 hours.

After completion of culturing, the culture filtrate is subjected to paper chromatography and colorimetric determination with ninhydrin to measure the amount of L-tryptophan produced.

As controls, the LA-105 strain and the LAR-1 strain are tested in the same manner. The results are shown in Table 4.

TABLE 4

| Strain | L-tryptophan (mg/ml) |
|---|---|
| LA-105 | — |
| LA-105/pTrp2-3 (K20, ATCC 39035) | 0.34 |
| LAR-1 | 0.48 |
| LAR-1/pTrp4-3 (K31, TCC 39280) | 1.12 |

EXAMPLE 5

Cloning of a gene responsible for the biosynthesis of L-histidine of *Corynebacterium glutamicum* C156 and production of L-histidine by the expression of the gene in *Corynebacterium glutamicum*, *Corynebacterium herculis*, *Brevibacterium flavum* and *Brevibacterium lactofermentum*:

1) Preparation of a chromosomal DNA of *Corynebacterium glutamicum* C156 and plasmid pCG11.

A chromosomal DNA is prepared by the same method as in Example 1 (1) from *Corynebacterium glutamicum* C156 (FERM P-6910) which is resistant to 1,2,4-triazole-3-alanine and capable of producing histidine.

Separately, pCG11, to be used as a vector plasmid, is isolated from the LA103 strain derived from *Corynebacterium glutamicum* L-22 and containing pCG11, i.e. LA103/pCG11 (ATCC 39022) by the same method as in Example 1 (1).

2) Cloning of a gene responsible for the biosynthesis of histidine of *Corynebacterium glutamicum* C156.

In this step, 10 units of BglII (product of Takara Shuzo Co.) is added to 200 μl of a reaction solution for the restriction enzyme BglII consisting of 10 mM Tris (pH 7.5), 7 mM $MgCl_2$, 60 mM NaCl and 7 mM 2-mercaptoethanol and containing 3 μg of plasmid pCG11 DNA prepared as above and 9 μg of the chromosomal DNA obtained as above. The mixture is allowed to react at 37° C. for 60 minutes and the reaction is stopped by heating at 65° C. for 10 minutes. To the mixed digest, 40 μl of a buffer solution for T4 ligase (pH 7.6) consisting of 200 mM Tris, 66 mM $MgCl_2$ and 100 mM dithiothreitol, 40 μl of 5 mM ATP solution, 0.3 μl of T4 ligase (product of Takara Shuzo Co., 1 unit/μl) and 120 μl of water are added. Reaction is carried out at 12° C. for 16 hours.

The T4 ligase reaction mixture is used for the transformation of *Corynebacterium glutamicum* LH33 which requires histidine for growth and is sensitive to lysozyme.

The transformation is carried out using protoplasts of the LH33 strain. The protoplasts are prepared by the same method as in Example 1 (2). Then, 0.5 ml of a protoplast suspension is put in a small test tube and subjected to centrifugation at 2,500× g for 5 minutes. The protoplasts are resuspended in 1 ml of TSMC buffer solution (pH 7.5) consisting of 10 mM magnesium chloride, 30 mM calcium chloride, 50 mM Tris and 400 mM sucrose and subjected to centrifugation and washing. The resultant precipitate is resuspended in 0.1 ml of TSMC buffer solution. Then, 100 μl of a mixture of two-fold concentrated TSMC buffer solution and the ligated DNA mixture mentioned above (1:1) is added to the suspension, followed by addition of 0.8 ml of TSMC buffer solution containing 20% PEG6,000. After three minutes, 2 ml of RCGP medium (pH 7.2) is added and the mixture is subjected to centrifugation at 2,500× g for 5 minutes to remove supernatant fluid. The precipitated protoplasts are suspended in 1 ml of RCGP medium and 0.2 ml of the suspension is spread on RCGP agar medium (pH 7.2) which contains 400 μg/ml spectinomycin and 1.4% agar. Culturing is carried out at 30° C. for 7 days.

Spectinomycin-resistant colonies grown on the selection medium are collected and washed with physiological saline solution and centrifuged twice. The precipitate is spread on a minimum agar medium M1 containing 100 μg/ml spectinomycin and culturing is carried out at 30° C. for 2 days to select transformants which are resistant to spectinomycin and do not require histidine for growth.

A plasmid is isolated from one of these transformants by ethidium bromide-cesium chloride density gradient centrifugation as in Example 1(1). The plasmid is digested or double-digested with various restriction enzymes and the resulting DNA fragments are analyzed by agarose gel electrophoresis to determine the restriction pattern of the plasmid DNA, which is named pPH8. pPH8 has a structure wherein a DNA fragment of about 10.6 Kb is inserted in the BglII site of pCG11.

pPH8 DNA is used for the retransformation of the H33 strain (FERM P-6909) which is the parent strain of the LH33 strain and requires histidine for growth and is resistant to lysozyme. None of the spectinomycin-resistant transformants obtained require histidine for growth, indicating that genes encoding enzymes involved in the biosynthesis of histidine of the histidine-producing C156 strain are cloned in the plasmid.

Cloning of genes encoding enzymes involved in the biosynthesis of histidine can also be carried out using the H33 strain as a host.

3) Production of L-histidine by *Corynebacterium glutamicum* carrying pPH8

*Corynebacterium glutamicum* LA-103 (FERM P-5947, ATCC 31866) is transformed with pPH8 DNA and a transformant resistant to spectinomycin is selected on an RCGP agar medium containing 400 μg/ml spectinomycin. The transformant is purified and the plasmid is isolated and analyzed to determine the structure, whereby the plasmid is confirmed to have the same structure as that of pPH8.

*Corynebacterium glutamicum* LA103/pPH8 containing pPH8 has been deposited with the American Type Culture Collection, U.S.A. as *Corynebacterium glutamicum* K32, ATCC 39281.

*Corynebacterium glutamicum* LA103/pCG11 (ATCC 39022) and *Corynebacterium glutamicum* LA103/pPH8 (ATCC 39281) are tested for L-histidine production in the following manner.

The two strains are cultured in NB agar medium at 30° C. overnight and a loopful of the cells is inoculated in 5 ml of a production medium P5 (adjusted to pH 7.4 with ammonia) consisting of 12% molasses (as sugar), 0.2% $KH_2PO_4$, 0.1% $K_2HPO_4$, 0.05% $MgSO_4.7H_2O$, 0.25% NaCl, 2.3% $(NH_4)_2SO_4$, 0.2% urea and 2% $CaCO_3$ and containing 200 μg/ml arginine and 200 μg/ml methionine. Culturing is carried out at 30° C. for 75 hours and the amount of L-histidine in the medium is determined by the colorimetric method using sulfanilic acid (Pauly) reagent of H. Pauly, Hoppe-Seylers: Z. Physiolo. Chem., 42, 508 (1904), ibid. 94, 284 (1915). The results are shown in Table 5.

TABLE 5

| Strain | L-histidine (mg/ml) |
|---|---|
| LA-103/pCG11 | 0 |
| LA-103/pPH8 (K32) | 2.6 |

4) Production of L-histidine by *Corynebacterium herculis*, *Brevibacterium flavum* and *Brevibacterium glutamicum* carrying pPH8.

*Corynebacterium herculis* ATCC 13868, *Brevibacterium flavum* ATCC 14067 and *Brevibacterium lactofermentum* ATCC 13869 are transformed with pPH8.

Each strain is grown in SSM medium and 0.3 units/ml penicillin G is added at an $OD_{660}$ value of 0.2. Culturing is continued and cells are collected at an $OD_{660}$ value of 0.6. The cells are treated in RCGP medium containing 1 mg/ml lysozyme by the same method as mentioned above to form protoplasts. Transformation is carried out using pPH8 as mentioned above and transformants are selected as colonies grown on RCGP agar medium containing 400 μg/ml spectinomycin.

The transformants resistant to spectinomycin are purified and plasmid DNAs are prepared from the cultured cells thereof according to the method of Japanese Published Unexamined Patent Application Nos. 183799/82 and 134500/82. By analysis of the restriction enzyme cleavage pattern it is confirmed that the plasmids have the same structure as that of pPH8, establishing that plasmid pPH8 derived from plasmid pCG11 is replicable in *Corynebacterium herculis*, *Brevibacterium flavum* and *Brevibacterium lactofermentum* and that plasmid pCG11 is broadly applicable to these bacteria.

Strains containing pPH8, *Corynebacterium herculis* K33, *Brevibacterium flavum* K34 and *Brevibacterium lactofermentum* K35 have been deposited with the American Type Culture Collection, U.S.A. as ATCC 39282, 39283 and 39284 respectively.

These strains are tested for L-histidine production in the following manner. Strains harboring plasmid pPH8 and the parent strains thereof are cultured on NB agar medium at 30° C. overnight and a loopful of the cells is inoculated in 5 ml of P5 medium. Culturing is carried out with shaking at 30° C. for 75 hours and the amount of L-histidine in the medium is determined colorimetrically by the above-mentioned method of Pauly. The results are shown in Table 6.

TABLE 6

| Strain | L-histidine (mg/ml) |
| --- | --- |
| ATCC 13868 | 0 |
| ATCC 13868/pPH8 (K33, ATCC 39282) | 2.4 |
| ATCC 14067 | 0 |
| ATCC 14067/pPH8 (K34, ATCC 39283) | 3.0 |
| ATCC 13869 | 0 |
| ATCC 13869/pPH8 (K35, ATCC 39284) | 2.0 |

The above results show that genes responsible for the production of histidine in *Corynebacterium glutamicum* are expressed in other bacteria such as *Corynebacterium herculis*, *Brevibacterium flavum* and *Brevibacterium lactofermentum* and contribute to the production of histidine.

EXAMPLE 6

Preparation of plasmid pCB101

1) Isolation of pCG11 and pUB110

*Corynebacterium glutamicum* LA 103/pCG11 (ATCC 39022) containing pCG11 is cultured in 400 ml of NB medium to an OD value of about 0.8 and pCG11 is isolated from the cultured cells by the same method as in the isolation of pCG2 in Example 1 (1).

Plasmid pUB110 is isolated from the cultured cells of *Bacillus subtilis* BR 151/pUB110 described in Proc. Natl. Acad. Sci. USA, 75, 1423 (1978) by the method of Gryczan et al. J. Bacteriol. 134, 318 (1978).

2) In vitro recombination of pCG11 and pUB110

2 units of BglII (product of Takara Shuzo Co., 6 units/μl) is added to 100 μl of the BglII reaction buffer solution (pH 7.5) consisting of 10 mM Tris-hydrochloride, 7 mM MgCl$_2$, 60 mM NaCl and 7 mM 2-mercaptoethanol and containing 2 μg of pCG11 plasmid DNA. The mixture is allowed to react at 37° C. for 60 minutes. Separately, 2 units of BamHI (product of Takara Shuzo Co., 6 units/μl) is added to 100 μl of the BamHI reaction buffer solution (pH 8.0) consisting of 10 mM Tris-hydrochloride, 7 mM MgCl$_2$, 100 mM NaCl, 2 mM mercaptoethanol and 0.01% bovine serum albumin and containing 2 μg of pUB110 plasmid DNA. The mixture is allowed to react at 37° C. for 60 minutes.

Both digests are mixed and 40 μl of the T4 ligase buffer solution, 40 μl of 5 mM ATP, 0.2 μl of T4 ligase and 120 l of H$_2$O are added. The mixture is allowed to react at 12° C. for 16 hours. The reaction mixture is extracted twice with 400 μl of phenol saturated with TES buffer solution and the extract is subjected to dialysis against TES buffer solution to remove phenol.

3) Recovery of pCB101

*Corynebacterium glutamicum* LA 103 is transformed with 100 μl of the mixture of a two-fold concentrated TSMC buffer solution and the ligase reaction mixture mentioned above (1:1) and kanamycin-resistant strains are selected by the same method as in Example 1 (3). Colonies formed are replicated on NB agar medium containing 12.5 μg/ml kanamycin or 100 μg/ml spectinomycin. After culturing at 30° C. for 2 days, three transformants resistant to both drugs are selected at random and purified on the same agar medium. The three strains are grown in 400 μl of NB medium to an OD value of about 0.8. Cells are harvested and plasmids are isolated from the cells by ethidium bromide-cesium chloride density gradient centrifugation as described in Example 1 (1). The plasmid DNA (30 to 35 μg) is obtained from each transformant.

Figure 2:
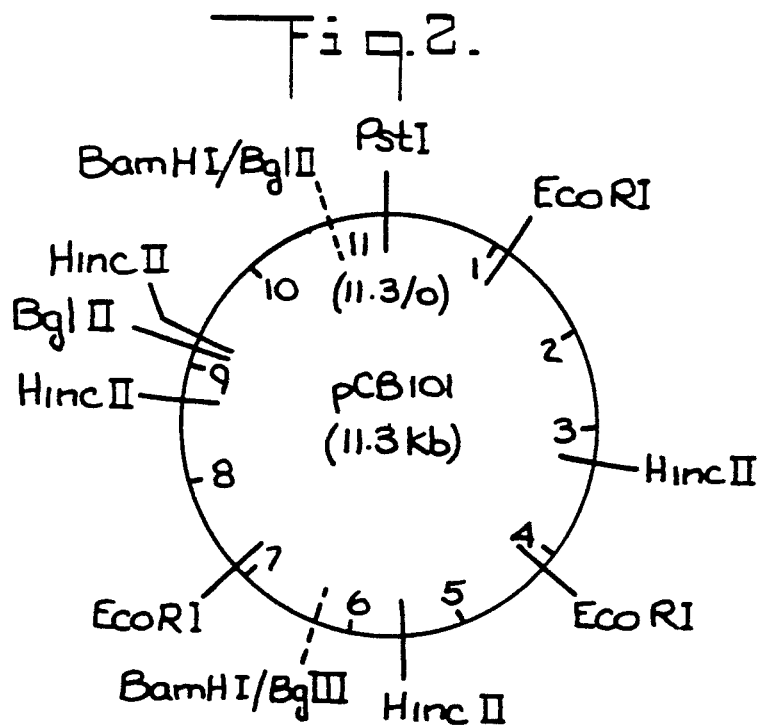
FIG. 2 is a cleavage map of the plasmid pCB101.

These plasmid DNAs are analyzed by digestion with restriction endonucleases and agarose gel electrophoresis to determine the molecular weights and the cleavage sites for PstI, EcoRI, HincII and BglII as in Example 1 (3). All of the three plasmids have the structure wherein pUB110 is ligated to pCG11 at BglII-generated cohesive ends which are compatible with those generated with BamHI. The structure of two of the plasmids is illustrated in FIG. 2 as pCB101 and the other has the opposite orientation of recombination.

Transformants with all of the plasmids have the resistance to Spec derived from pCG11 and that to Km derived from pUB110.

*Corynebacterium glutamicum* LA 103 is transformed with these plasmid DNAs. The resultant kanamycin-resistant transformants are endowed with spectinomycin-resistance and have the same plasmid as the donor plasmid characterized by the cleavage pattern by various restriction endonucleases.

What is claimed is:

1. A process for producing L-threonine which comprises the steps of culturing in a culture medium a Corynebacterium or Brevibacterium host microorganism harboring a recombinant DNA containing an *Escherichia coli* threonine operon inserted into a vector, accumulating L-threonine in the culture medium and thereafter recovering L-threonine therefrom.

2. The process according to claim 1, wherein the recombinant DNA is pEthr1 and has a cleavage map having two BamHI/BglII cleavage sites, one PstI cleavage site, one XhoI cleavage site and three EcoRI cleavage sites.

3. A process for producing L-glutamic acid which comprises the steps of culturing in a culture medium a Corynebacterium or Brevibacterium host microorganism harboring a recombinant DNA containing an *Escherichia coli phosphoenolpyruvic acid carboxylase gene inserted into a vector, accumulating L-glutamic acid in the culture medium and thereafter recovering L-glutamic acid therefrom.

4. The process according to claim 3, wherein the recombinant DNA is pEppc1.

5. Corynebacterium glutamicum K18, ATCC 39033.

6. Corynebacterium glutamicum K19, ATCC 39034.

7. A process for producing L-lysine which comprises culturing in a medium a microorganism obtained by transforming a host Corynebacterium or Brevibacterium microorganism which is sensitive to S-(2-aminoethyl)-cysteine with a recombinant DNA wherein a DNA fragment conferring resistance to S-(2-aminoethyl)-cysteine and lysine producing ability is inserted into a vector DNA, accumulating L-lysine in the culture medium and recovering L-lysine therefrom.

8. The process according to claim 7, wherein the recombinant DNA is plasmid pAec5.

9. Corynebacterium glutamicum K17, ATCC 39032.

* * * * *

UNITED STATES PATENT AND TRADEMARK OFFICE
CERTIFICATE OF CORRECTION

PATENT NO. : 5,236,831
DATED : August 17, 1993
INVENTOR(S) : RYOICHI KATSUMATA, ET AL.

Page 1 of 3

It is certified that error appears in the above-identified patent and that said Letters Patent is hereby corrected as shown below:

Title page,
IN [54] TITLE, and col. 1, line 2,

"BRERIBACTERIA" should read --BREVIBACTERIA--.

Title page,
IN [73] ASSIGNEE

"Kiowa Hakko Kogyo Co., Ltd.," should read
--Kyowa Hakko Kogyo Co., Ltd.,--.

COLUMN 1

Line 3, "BRERIBACTERIA" should read --BREVIBACTERIA--.

COLUMN 2

Line 27, "furthermore" should read --furtherance--.

COLUMN 3

Line 1, "the all" should read --all the--.
Line 21, "pEthrl U.S." should read --pEthrl (U.S.--.
Line 22, "Dec. 16, 1982." should read --Dec. 16, 1982).--.

COLUMN 4

Line 26, "tetracycline," should read --tetracycline, 2-15 µg/ml chloramphinicol or 2-25 µg/ml kanamycin.--.

COLUMN 6

Line 19, "transformant;" should read --transformant.--.

UNITED STATES PATENT AND TRADEMARK OFFICE
CERTIFICATE OF CORRECTION

PATENT NO. : 5,236,831
DATED : August 17, 1993
INVENTOR(S) : RYOICHI KATSUMATA, ET AL.

It is certified that error appears in the above-identified patent and that said Letters Patent is hereby corrected as shown below:

COLUMN 7

Line 33, "2." should read --2)--.
Line 53, "3." should read --3)--.

COLUMN 8

Line 34, "Bacilus" should read --Bacillus--.
Line 52, "homolgous" should read --homologous--.

COLUMN 9

Line 52, "cose" should read --cose,--.

COLUMN 14

Line 15, "tranformants." should read --transformants.--.
Line 52, "2." should read --2)--.

COLUMN 15

Line 1, "3." should read --3)--.
Line 42, "Sa;lI" should read --SalI-- and "Cpo.)" should read --Co.)--.

COLUMN 16

Line 10, "form" should read --from--.
Line 23, "show" should read --shows--.

COLUMN 17

Line 3, "2." should read --2)--.

UNITED STATES PATENT AND TRADEMARK OFFICE
CERTIFICATE OF CORRECTION

PATENT NO. : 5,236,831
DATED : August 17, 1993
INVENTOR(S) : RYOICHI KATSUMATA, ET AL.

Page 3 of 3

It is certified that error appears in the above-identified patent and that said Letters Patent is hereby corrected as shown below:

COLUMN 18

Line 64, "aqueous" should be deleted.

COLUMN 24

Line 60, "*glutamicum*" should read --*lactofermentum*--.

Signed and Sealed this

First Day of November, 1994

Attest:

BRUCE LEHMAN

Attesting Officer

Commissioner of Patents and Trademarks